US008183400B2

(12) United States Patent
Szul et al.

(10) Patent No.: US 8,183,400 B2
(45) Date of Patent: May 22, 2012

(54) ALKYLENE OXIDE RECOVERY SYSTEMS (75) Inventors: John F. Szul, Hurricane, WV (US);
James H. Mccain, Charleston, WV (US); Floyd L. Pfeffer, Midland, MI (US); Harvey E. Andresen, Luling, LA (US); Phillip R. Fairchild, Luling, LA (US); Kent E. Newman, Scott Depot, WV (US)

(73) Assignee: Dow Technology Investments LLC, Midland, MI (US)

( * ) Notice: Subject to any disclaimer, the term of this patent is extended or adjusted under 35 U.S.C. 154(b) by 438 days.

(21) Appl. No.: 12/460,755

(22) Filed: Jul. 24, 2009

(65) Prior Publication Data
US 2010/0029964 A1 Feb. 4, 2010

Related U.S. Application Data (60) Provisional application No. 61/137,494, filed on Jul. 31, 2008, provisional application No. 61/137,493, filed on Jul. 31, 2008, provisional application No. 61/137,517, filed on Jul. 31, 2008, provisional application No. 61/137,514, filed on Jul. 31, 2008, provisional application No. 61/137,485, filed on Jul. 31, 2008.

(51) Int. Cl.
*C07D 301/32* (2006.01)
*B01D 3/26* (2006.01)
*B01D 3/38* (2006.01)

(52) U.S. Cl. .......... 549/541; 203/83; 202/197; 568/679; 568/680

(58) Field of Classification Search .................. 549/541; 203/83; 202/197
See application file for complete search history.

(56) References Cited

U.S. PATENT DOCUMENTS

| 2,615,901 | A | 10/1952 | McClellan |
|---|---|---|---|
| 2,697,104 | A | 12/1954 | Lowe et al. |
| 2,771,473 | A | 11/1956 | Courter |
| 2,775,600 | A | 12/1956 | Maslan |
| 2,815,650 | A | 12/1957 | McIntire et al. |
| 3,094,401 | A | 6/1963 | Lidell |
| 3,165,539 | A | 1/1965 | Lutz |
| 3,174,262 | A | 3/1965 | Lutz |
| 3,216,177 | A | 11/1965 | Bracken et al. |
| 3,398,062 | A | 8/1968 | Tsao |
| 3,418,338 | A | 12/1968 | Gilman et al. |
| 3,531,376 | A | 9/1970 | Minoda et al. |
| 3,729,899 | A | 5/1973 | Cunningham |
| 3,745,092 | A | 7/1973 | Vanderwater |
| 3,766,714 | A | 10/1973 | Cunningham et al. |
| 3,867,113 | A | 2/1975 | Foster et al. |
| 3,904,656 | A | 9/1975 | Broz |
| 3,948,621 | A | 4/1976 | Cocuzza et al. |
| 3,964,980 | A | 6/1976 | Ozero |
| 4,033,617 | A | 7/1977 | Cocuzza et al. |
| 4,134,797 | A | 1/1979 | Ozero |
| 4,597,833 | A | 7/1986 | N'eel et al. |
| 4,845,296 | A | 7/1989 | Ahmed et al. |
| 4,966,657 | A | 10/1990 | Delannoy et al. |
| 4,983,260 | A | 1/1991 | N'eel et al. |
| 5,233,060 | A | 8/1993 | Pendergast et al. |
| 5,529,667 | A | 6/1996 | Coffey |
| 6,080,897 | A | 6/2000 | Kawabe |
| 6,123,812 | A | 9/2000 | Bessling et al. |
| 6,437,199 | B1 | 8/2002 | Oka et al. |
| 6,498,272 | B1 | 12/2002 | Schröder et al. |
| 6,833,057 | B1 | 12/2004 | Bessling et al. |
| 7,179,875 | B2 | 2/2007 | Fuchs et al. |
| 2004/0236049 | A1 | 11/2004 | Fuchs et al. |
| 2005/0103617 | A1 | 5/2005 | Andreis et al. |
| 2005/0277778 | A1 | 12/2005 | Viswanathan et al. |
| 2006/0264648 | A1 | 11/2006 | Beekman et al. |

FOREIGN PATENT DOCUMENTS

| CZ | 104663 | 8/1962 |
|---|---|---|
| DE | 1165567 | 3/1964 |
| DE | 199 24 533 | 11/2000 |
| DE | 19924533 | 11/2000 |
| DE | 101 38 150 | 2/2003 |
| DE | 10138150 | 2/2003 |
| EP | 0 181 273 | 5/1986 |
| EP | 0181273 | 5/1986 |
| FR | 1 330 900 | 5/1963 |
| FR | 1330900 | 5/1963 |
| FR | 2 851 564 | 8/2004 |
| FR | 2851564 | 8/2004 |
| GB | 564646 | 10/1944 |
| GB | 589547 | 6/1947 |
| JP | 54-16416 | 2/1979 |
| JP | 54016416 | 2/1979 |
| JP | 62-12770 | 1/1987 |
| JP | 62012770 | 1/1987 |
| WO | WO 03/055869 | 7/2003 |
| WO | WO 2004/056453 | 7/2004 |
| WO | WO 2006/120207 | 11/2006 |
| WO | WO 2009/094103 | 7/2009 |
| WO | WO 2009/105252 | 8/2009 |

OTHER PUBLICATIONS

International Search Report and Written Opinion from related PCT Application PCT/US 2009/004319, dated Jan. 27, 2010 (16 pgs).
Viera, G.A., et al. "Lessons Learned from the Ethylene Oxide Explosion at Seadrift, Texas". Chem Eng. Progess. 89 (8), pp. 66-75 (1993).
Wankat, P.C. et al. "Two-Feed Distillation: Same-Composition Feeds with Different Enthalpies" Ind. Eng. Chem. Res. 1993, 32, 3061-3067.
Cleveland et al. "Meteor Revolution" Hydrocarbon Engineering Oct. 2001 pp. 69-71.
Xiangyu, Z. "A Comparison of EO/EG Process Technologies" Sinopec Shanghai Engineering Co. Shanghai, 2006.

(Continued)

*Primary Examiner* — Bernard Dentz (74) *Attorney, Agent, or Firm* — Brooks, Cameron & Huebsch, PLLC (57) ABSTRACT Embodiments of the present disclosure include processes and systems for recovering alkylene oxide. System embodiments include a stripping section located in an alkylene oxide recovery column to convert a feed stream comprising to a first gas phase portion comprising alkylene oxide, a condensing zone comprising at least a first condenser and a second condenser configured in series, and a reabsorption region located in the alkylene oxide recovery column above the last of the at least two condensers.

20 Claims, 2 Drawing Sheets

OTHER PUBLICATIONS

"U.S. Appl. No. 12/460,810, Notice of Allowance mailed Dec. 7, 2011", 12 pages.

"U.S. Appl. No. 12/460,756, Non Final office action mailed Dec. 5, 2011", 15 pages.

"U.S. Appl. No. 12/460,752, Non Final office action mailed Dec. 13, 2011", 15 pages.

"U.S. Appl. No. 12/460,756, Response filed Mar. 5, 2012 for Non Final office action mailed Dec. 5, 2011", 10 pages.

"U.S. Appl. No. 12/460,775, Notice of Allowance mailed Jun. 8, 2011", 5 pages.

"U.S. Appl. No. 12/460,775, Notice of Allowance mailed Jul. 13, 2011", 5 pages.

ALKYLENE OXIDE RECOVERY SYSTEMS

This application claims priority to U.S. Provisional Application 61/137,494 filed Jul. 31, 2008, the specification of which is incorporated herein by reference, and is co-filed with co-owned U.S. Patent Application Ser. No. 61/137,493, entitled "Alkylene Oxide Recovery Systems" filed on Jul. 31, 2008, Ser. No. 61/137,517, entitled "Alkylene Oxide Recovery Systems" filed on Jul. 31, 2008, Ser. No. 61/137,514, entitled "Alkylene Oxide Purification Processes and Systems" filed on Jul. 31, 2008, Ser. No. 61/137,485, entitled "Alkylene Oxide Purification Systems" filed on Jul. 31, 2008.

FIELD OF THE DISCLOSURE

The present disclosure relates to improved processes and systems for recovering alkylene oxide from an aqueous solution containing the same. More specifically, the disclosure relates to processes and systems for recovering the alkylene oxide from a feed stream by stripping and reabsorbing alkylene oxide in a single Alkylene Oxide Recovery Column ("AORC").

BACKGROUND

Alkylene oxide is commercially important and manufactured in large quantities by partially oxidizing alkylene with an oxygen containing gas over a suitable catalyst at elevated temperatures and pressures (e.g., 2 to 25 atmospheres). The alkylene oxide is separated from the gaseous reaction effluent containing unreacted alkylene, oxygen, and other gaseous components of the reaction mixture (e.g., carbon dioxide, inert gases). Separation is typically achieved by scrubbing the alkylene oxide from the gaseous reaction mixture by means of water, which results in a gaseous reaction effluent and an aqueous alkylene oxide solution.

Recovery of the ethylene oxide from the gaseous reaction effluent can involve an initial water absorption step, followed by a stripping step, which is in turn followed by a reabsorption step. In some instances, each of the steps is carried out in separate distillation columns, which can lead to high equipment costs and safety concerns where areas of concentrated vapor phase or liquid phase ethylene oxide exist. One exemplary area where concentrated liquid phase ethylene oxide can exist is when vapor phase ethylene oxide coming out of the top of an ethylene oxide stripper is condensed, giving liquid ethylene oxide. The liquid ethylene oxide produced in the stripper can be transported to another piece of equipment to be further refined. However, handling and/or transporting concentrated ethylene oxide, for example, liquid ethylene oxide, can be dangerous due to the risk of contamination since contaminated liquid ethylene oxide can lead to a runaway polymerization which generates heat and can be explosively violent. As such, avoiding and/or alleviating the areas of concentrated and/or contaminated liquid ethylene oxide can increase safety in the recovery of ethylene oxide.

SUMMARY

Embodiments of the present disclosure provide processes and systems for recovering alkylene oxide from a feed stream. Embodiments can include a stripping section, a condensing zone with at least two condensers in series, and a reabsorption region in a single column, where the column includes one or more side take-offs, producing an alkylene oxide stream which can be directly fed to a glycol reactor.

In some embodiments, the present disclosure provides a process to produce purified alkylene oxide. The purified alkylene oxide produced can contain a very low content of aldehydic impurities, such as acetaldehyde, as compared to, for example, the content of aldehydic impurities in the purified alkylene oxide produced as described in U.S. Pat. No. 3,964,980. The process embodiments of the present disclosure also make it possible to recover increased yields of purified alkylene oxide as compared to an identical process but for the improvement of the present disclosure. The impurity reduction can minimize unwanted chemical reactions in the subsequent glycol reaction processes and can lead to improved ultraviolet absorbance and color in the purified glycol products. According to embodiments of the present disclosure, the steps of reabsorbing alkylene oxide and stripping carbon dioxide, oxygen, and other light gases are carried out in a single column including both stripping and reabsorption regions. The apparatus can also be used for other chemical processing systems that require reabsorption and stripping.

As discussed herein, process embodiments for the recovery of alkylene oxide are provided. The process includes introducing a feed stream containing alkylene oxide to a stripping section of an alkylene oxide recovery column. The alkylene oxide recovery column includes the stripping section, a condensing zone, and a reabsorption region. The condensing zone further includes at least a first condenser and a second condenser configured in series above the stripping section. The process also includes stripping at least a portion of alkylene oxide from the feed stream to form a first gas phase portion that flows from the stripping section to the reabsorption region through the condensing zone. The process further includes partially and progressively condensing the first gas phase portion in the first condenser into a liquid reflux stream and a second gas phase portion. The second gas phase portion is condensed in the second condenser into an alkylene oxide rich vapor stream and a first aqueous solution. The second condenser further includes a first take-off to remove the first aqueous solution from the condensing zone. The process further includes reabsorbing at least some of the alkylene oxide rich vapor stream into an aqueous stream to form a second aqueous solution in the reabsorption region. The reabsorption region further includes a second take-off to remove the second aqueous solution from the reabsorption region.

In yet another embodiment, a system to recover alkylene oxide is provided. The system includes a stripping section located in an alkylene oxide recovery column to convert a feed stream to a first gas phase portion comprising alkylene oxide. The system further includes a condensing zone with at least a first condenser and a second condenser configured in series to partially and progressively condense the first gas phase portion of the feed stream. The first condenser partially condenses the first gas phase portion to produce a liquid reflux stream and a second gas phase portion including alkylene oxide, water, and light gases. The second condenser partially condenses the second gas phase portion to produce an alkylene oxide rich vapor stream and a first aqueous solution comprising alkylene oxide, water, and light gases. The system further includes a reabsorption region in the alkylene oxide recovery column above the last of the at least two condensers to reabsorb alkylene oxide from the alkylene oxide rich vapor stream to form a second aqueous solution comprising alkylene oxide, water, and light gases. The reabsorption region further includes an inlet to introduce a water stream. The system further includes at least one gas inlet to introduce a gaseous stream to at least one of the second condenser and the reabsorption region to strip light gases, from at least one of the first aqueous solution and the second aqueous solution, to form at least one of a first and second gas phase light impurity fraction.

In another embodiment, the system to recover alkylene oxide includes an upper take-off on the alkylene oxide recovery column to remove one or more gas phase light impurity fractions.

In yet another aspect the alkylene oxide recovered is selected from ethylene oxide or propylene oxide.

DEFINITIONS

The term "alkylene oxide recovery column," or "column" refers to, for example, a generally upright, cylindrical column or tower containing separation stages, where the separation stages provide a surface area for a liquid and a gas to come into contact, facilitating mass transfer between the liquid and the gas. The column can also have other shapes and general orientations including, but not limited to, a polygonal shaped column that is positioned in horizontal orientation. The alkylene oxide recovery column comprises a stripping section, a condensing zone, and a reabsorption region.

As used herein a "separation stage" is defined as a volume, device or combination of devices in a distillation apparatus within or at which phases are brought into intimate contact, where mass transfer occurs between the phases tending to bring them to equilibrium, and where the phases can then mechanically separated. For the various embodiments, each tray of a tray tower and/or packing of a packed tower having a height equivalent to a theoretical plate ("HETP") is a separation stage, as these are the locations where fluids are brought into intimate contact, interphase diffusion occurs, and the fluids are separated. As such, the number of trays in a distillation apparatus can also be attributed to an equivalent number of separation stages that are obtained by using packing. For the various embodiments, the terms separation stage, tray and/or packing having a HETP can be used interchangeably, unless otherwise stated to the contrary.

As appreciated by one skill in the art, determining a number of equilibrium stages (theoretical trays) for use in a distillation apparatus can be calculated based on the material balances and equilibrium considerations of the compounds (e.g., ethylene oxide, water, and other compounds in liquid form) to be separated in the substance (e.g., the aqueous mixture of the present disclosure). The efficiency of the separation stage, and therefore the number of separation stages that are actually used, can be determined by the mechanical design used and the condition of operation for the distillation apparatus. For the various embodiments provided herein, the number of equilibrium stages (or theoretical trays) could be used in place of the number of separation stages provided in the present disclosure through the use of the efficiency of the separation stage of the distillation apparatus.

As used herein, the term "stripping section" refers to the portion of the column where one or more components of the feed stream are removed by being placed in contact with a gas stream that is insoluble in the aqueous solution or by heating the aqueous solution to cause a phase change in one or more components to be removed. In the embodiments discussed herein, stripping can be performed on an aqueous solution, or feed stream, to purify, recover, and/or separate alkylene oxide. The "feed stream" can include a mixture of alkylene oxide and water. The feed stream can also include unreacted alkylene, methane, carbon dioxide, oxygen, and trace impurities. In certain embodiments, the feed stream is of two phases, a liquid phase and a vapor phase.

As used herein, the "condensing zone" refers to the portion of the column where at least two condensers are configured in series above the stripping section. A "condenser" is a device that converts vapor into liquid. In the embodiments discussed here in, a gas phase portion of the feed stream can enter the condenser. At least some portion of the gas phase portion of the feed stream condenses into liquid while the remainder of the gas phase portion passes through the condenser and remains in gas phase. A "reflux condenser" is a condenser where the vapor over a boiling liquid condenses and flows back into vessel containing the boiling liquid to prevent the vessel's contents from boiling dry.

As used herein, "reabsorption region" refers to the portion of the column where some components of a gas are removed by contacting the gas with a solvent that absorbs some components of the gas while not absorbing others.

In some embodiments of the present disclosure, the alkylene oxide recovery column includes a condensing zone integral with the column in the upper portion of the stripping section. As used herein, a condenser "integral with the column" refers to a condenser that is positioned inside the external walls of the column. In some embodiments, the condensers can be external to the column with appropriate connections to the column for exchange of materials to and from the condensers.

As used herein, "a," "an," "the," "at least one," and "one or more" are used interchangeably. The terms "comprises" and variations thereof do not have a limiting meaning where these terms appear in the description and claims. Thus, for example, a stripping section located in an ethylene oxide recovery column to convert a portion of "a" feed stream to a gas phase portion can be interpreted to mean that the ethylene oxide recovery column includes "one or more" feed streams.

The term "and/or" means one, more than one, or all of the listed elements.

As used herein, the term "about" may not be limited to the precise value specified. In at least one instance, the variance indicated by the term "about" can be determined with reference to the precision of the measuring instrumentation. As used herein, the term "approximately" is used synonymously with the term "about".

Also herein, the recitations of numerical ranges by endpoints include all numbers subsumed within that range (e.g., 1 to 5 includes 1, 1.5, 2, 2.75, 3, 3.80, 4, 5, etc.).

BRIEF DESCRIPTION OF THE DRAWINGS

In the accompanying drawings, like characters represent like parts throughout the drawings, wherein.

DETAILED DESCRIPTION

The present disclosure provides improved processes and systems for recovering alkylene oxide from a feed stream. While the embodiments herein provide for processes and systems for recovering alkylene oxide from a feed stream containing the alkylene oxide, a representative example of ethylene oxide will be discussed herein. However, one of skill in the art will appreciate that embodiments of the present disclosure may also apply to other alkylene oxides including propylene oxide, butylene oxide, methylene oxide, among others.

Before ethylene oxide can be recovered in an ethylene oxide recovery column, several steps can be performed to obtain the aqueous stream that is used as the feed stream. As described herein, the steps to produce alkylene oxide and to use alkylene oxide in further reactions can occur in one place, for example, in an alkylene oxide processing plant. The various steps, however, can also occur in separate facilities.

In addition, in an alkylene oxide production unit, the alkylene oxide production processes can be interlinked with alkylene oxide recovery processes. In certain cases where the alkylene oxide production unit is operated along with downstream product manufacturing units such as, for example, an alkylene glycol manufacturing unit, the alkylene oxide processes can also be interlinked with ethylene glycol manufacturing processes to maximize energy utilization, which in turn can lower production costs.

Alkylenes (olefins) employed in the process of this disclosure can be characterized by the following structural formula (I):

wherein $R_1$ and $R_2$ are each individually selected from hydrogen and lower monovalent radicals, preferably $C_1$-$C_6$ alkyl radicals including methyl, ethyl, propyl, butyl, and higher homologues having up to six carbon atoms. Preferably, $R_1$ and $R_2$ are each individually selected from hydrogen, methyl, and ethyl. More preferably, each $R_1$ and $R_2$ is hydrogen, and the preferred olefin is ethylene. The corresponding alkylene oxides produced in the process of this disclosure are preferably characterized by the following structural formula (II):

wherein $R_1$ and $R_2$ are identified herein in connection with the reactant olefin. Most preferably, the alkylene oxide is ethylene oxide (i.e., $R_1$ and $R_2$ are both hydrogen).

Oxygen may be provided to the process as pure molecular oxygen. Alternatively, oxygen may be provided as an oxygen-containing gas, where the gas further contains one or more gaseous components, for example, gaseous diluents such as nitrogen, helium, methane, and argon, which are essentially inert with respect to the oxidation process. In some embodiments, a suitable oxygen-containing gas is air. Additionally, the oxygen-containing gas may contain one or more of the following gaseous components: water, carbon dioxide, and various gaseous promoters and/or gaseous by-product inhibitors, as discussed herein.

The relative volumetric ratio of alkylene to oxygen in the feed stock gas may range in accordance with known values. Typically, the volumetric ratio of alkylene to oxygen in the feed stock may vary from about 2:1 to about 6:1. Likewise, the quantity of inert gases, diluents, or other gaseous components such as water, carbon dioxide, and gaseous promoters and gaseous by-product inhibitors, may vary in accordance with known conventional ranges as found in the art.

The present disclosure is applicable to epoxidation reactions in any suitable reactor, for example, fixed bed reactors, fixed bed tubular reactors, continuous stirred tank reactors (CSTRs), and fluid bed reactors, a wide variety of which are well known in the art. The desirability of recycling unreacted feed, employing a single-pass system, or using successive reactions to increase ethylene conversion by employing reactors in a series arrangement can also be readily determined by those skilled in the art.

The particular mode of operations selected can be dictated by process economics. Conversion of alkylene (olefin), preferably ethylene, to alkylene oxide, preferably ethylene oxide, can be carried out, for example, by continuously introducing a feed stream containing alkylene (e.g., ethylene) and oxygen, or an oxygen-containing gas, to a catalyst-containing reactor at a temperature of from about two hundred (200) degrees Celsius (° C.) to about three hundred (300)° C., and a pressure which may be in a range of from about five (5) atmospheres (gauge pressure) (five hundred six (506) kilopascals (kPa)) to about thirty atmospheres (gauge pressure) (3,040 kPa) depending on the mass velocity and productivity desired. Residence times in large scale reactors can be on the order of about 0.1 to about five (5) seconds. The resulting alkylene oxide, preferably ethylene oxide, can then be separated and recovered from the reaction products using further processes.

The alkylene oxide produced according to the present disclosure may be converted into alkylene glycols, alkanolamines, and glycol ethers. For example, ethylene glycol can be used in two applications: as a raw material for poly(ethylene terephthalate) for use in polyester fiber, film, and containers, and as an automotive antifreeze. Also, di-, tri-, and tetraethylene glycols are coproducts of ethylene glycol.

Ethylene glycol can be produced by the (catalyzed or uncatalyzed) hydrolysis of ethylene oxide. Ethylene oxide hydrolysis can proceed with either acid or base catalysis or uncatalyzed in neutral medium. Acid catalyzed hydrolysis activates the ethylene oxide by protonation for the reaction with water. Base catalyzed hydrolysis, however, results in considerably lower selectivity to ethylene glycol, producing diethylene glycol and higher glycols (e.g., triethylene and tetraethylene glycols) in addition to the ethylene glycol. Ethylene glycol monoethers can be manufactured by the reaction of an alcohol with ethylene oxide. Also, ethanolamine can be manufactured by the reaction of ethylene oxide with ammonia. See, for example, U.S. Pat. No. 4,845,296.

In some embodiments, the per-pass conversion of ethylene to ethylene oxide can be low (i.e., on the order of one (1) percent or less). The gaseous reaction effluent thus formed contains dilute concentrations of ethylene oxide along with unreacted ethylene and oxygen, aldehydes, acidic impurities, nitrogen, and argon, among other components. In some embodiments, the aldehydes can include formaldehyde and acetaldehyde. In some embodiments, the per-pass conversion of ethylene to ethylene oxide can range from five (5) percent to twenty-five (25) percent.

The ethylene oxide can be separated and recovered from the gaseous reaction effluent. For example, the gaseous reaction effluent from the reactor can be scrubbed with an absorbent, such as water, to form an aqueous mixture containing ethylene oxide in an absorber column. The absorption of ethylene oxide in water can recover ethylene oxide from unreacted ethylene, oxygen, and/or other gaseous components (e.g., carbon dioxide, nitrogen, argon). The remaining gaseous materials can then be recycled as cycle gas to be mixed with the feedstock of ethylene and oxygen and fed to the ethylene oxide reactor for the production of ethylene oxide as gaseous reaction effluent.

The aqueous mixture containing ethylene oxide from the absorber column can then be passed to the ethylene oxide recovery column of the present disclosure, where the aqueous mixture, or as used herein, the feed stream, is used to produce an ethylene oxide stream with a higher ethylene oxide weight percent. The ethylene oxide stream can be removed from the column and passed to other equipment in the ethylene oxide processing plant for further purification or for use in other reactions. For example, in some embodiments, the ethylene oxide stream can be routed to a glycol unit reactor, where ethylene oxide is converted to ethylene glycol by reaction with water. The ethylene glycol produced can be monoethylene glycol, diethylene glycol, and/or triethylene glycol.

In the Figures herein, as will be appreciated, elements shown in the embodiment herein can be added, exchanged, and/or eliminated so as to provide any number of additional embodiments. In addition, as will be appreciated the proportion and the relative scale of the elements provided in the figures are intended to illustrate the embodiments of the present disclosure, and should not be taken in a limiting sense. The Figures herein follow a numbering convention in which the first digit or digits correspond to the drawing Figure number and the remaining digits identify an element or component in the drawing. Similar elements or components between different figures may be identified by the use of similar digits. For example, 110 may reference element "10" in FIG. 1, and a similar element may be referenced as 210 in FIG. 2. In addition, the description herein of an element and/or component provided for one or more Figures is applicable to and associated with other Figures illustrating the same element and/or component number but which do not necessarily provide the express description thereof. So, for example, when element "10" in FIG. 1 is expressly discussed herein this express discussion is also applicable to element "10" in the other Figs. where it may appear.

Figure 1:
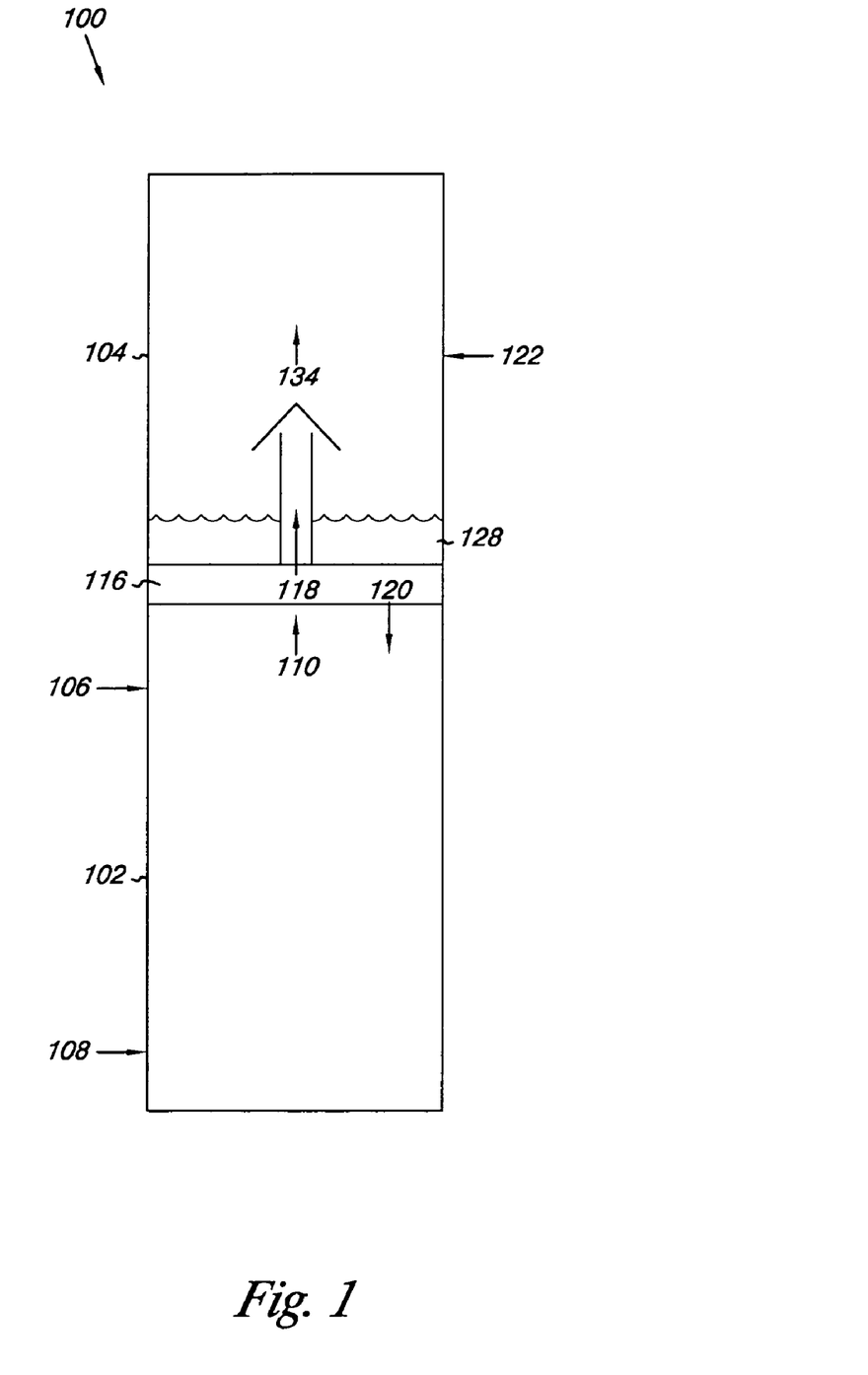
FIG. 1 illustrates a schematic representation of a system for recovery of alkylene oxide.

FIG. 1 illustrates a schematic representation of an ethylene oxide recovery column 100 for the recovery of ethylene oxide from a feed stream 106 containing ethylene oxide, the details of which may be found in the U.S. Provisional Application No. 61/137,493, entitled "Alkylene Oxide Recovery Systems" filed on the same date herewith, the contents of which are incorporated herein by reference. The alkylene oxide recovery column 100 includes a stripping section 102 and a reabsorption section 104.

Briefly, in the stripping section 102, the feed stream 106 containing alkylene oxide is introduced. The feed stream 106 makes contact in a countercurrent fashion with a second stripping gas 108 to convert a portion of the feed stream 106 to a gas phase portion 110. The gas phase portion 110 of the feed stream 106 flows from the stripping section 102 to a condenser 116 to cool and partially condense the gas phase portion 110 to produce an ethylene oxide rich vapor stream 118 and a liquid reflux stream 120. The alkylene oxide rich vapor stream 118 flows from the condenser 116 to the reabsorption section 104 of the column 100. The reabsorption section 104 absorbs alkylene oxide from the alkylene oxide rich vapor stream 118 by contacting the alkylene oxide rich vapor stream 118 with a water stream 122 to form an aqueous solution 128. A first stripping gas is provided in the reabsorption portion 104 to remove carbon dioxide and oxygen from the aqueous solution 128 as a light impurity fraction 134. The light impurity fraction 134 formed can be removed from an upper portion of the column 100.

The aqueous solution 128, in some embodiments is directed to a glycol unit for the conversion of alkylene oxide (e.g., ethylene oxide) to alkylene glycol (e.g., ethylene glycol). In certain embodiments, the aqueous solution 128 may be sent to an alkylene oxide purification column for further removal of impurities.

Figure 2:
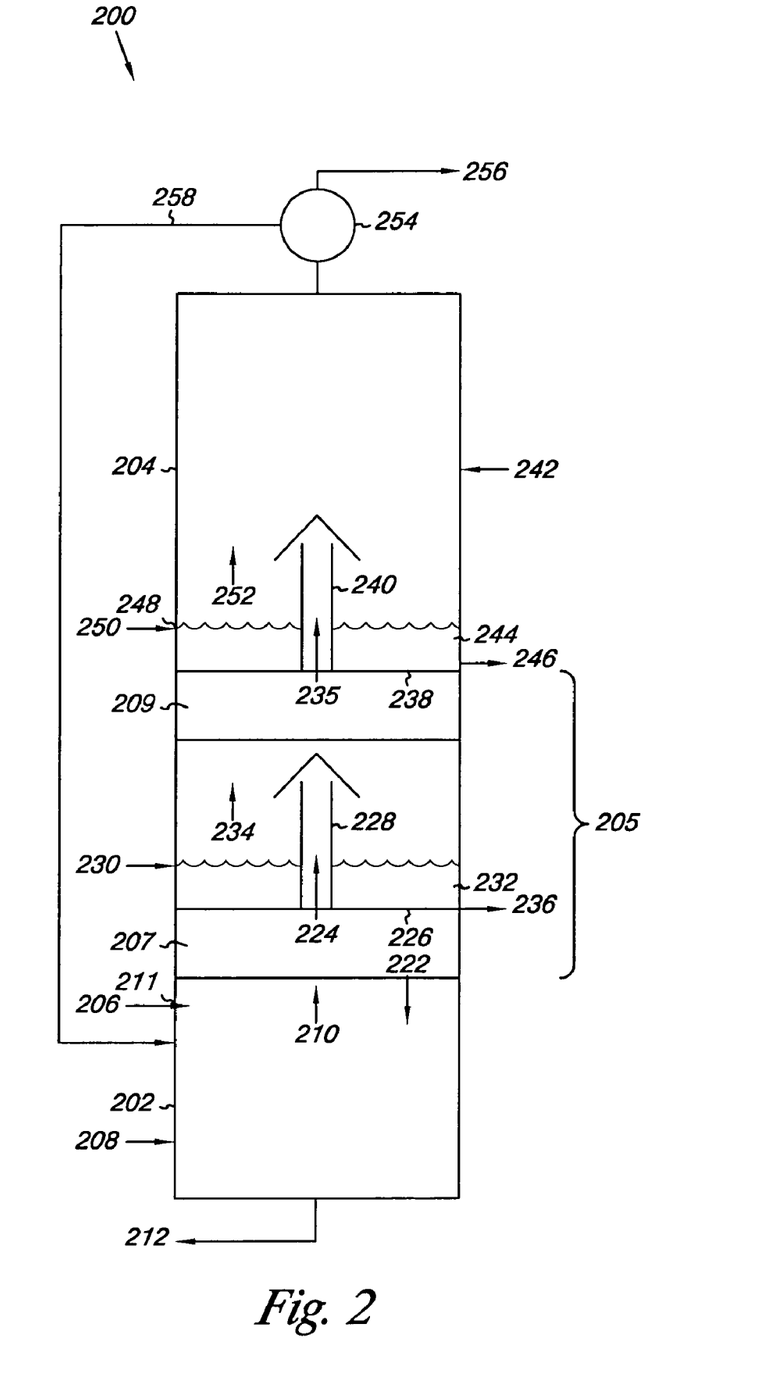
FIG. 2 illustrates an exemplary system for recovery of alkylene oxide in accordance with embodiments of the present disclosure.

FIG. 2 is an illustration of an alkylene oxide recovery column 200, or column 200, according to embodiments of the present disclosure. The alkylene oxide recovery column 200 includes a stripping section 202, a condensing zone 205, and a reabsorption region 204. The use of a single column to perform the stripping, condensing, and reabsorption, in some embodiments, results in lower equipment cost when building an alkylene oxide processing plant. Capital savings can be achieved by combining two or more columns and multiple unit operations into a single column, resulting in a significant reduction in bulk including minimization of instrumentation, controls, pumps, piping, and plot space.

The use of single column can also reduce the safety concerns by reducing the areas of concentrated vapor phase or liquid phase alkylene oxide. For instance, by performing the stripping, condensing, and reabsorbing steps in a single column rather than in more than one column, the alkylene oxide rich vapor stream can pass from the condenser or condensers to the reabsorption region rather than being transported to a separate column for further processing. The overall safety of the alkylene oxide process can be increased by reducing the transportation of pure or concentrated alkylene oxide, a difficult material to handle in terms of its flammability and volatility.

The alkylene oxide recovery column 200, as discussed herein, can be configured to be of any shape and orientation. For example, in some embodiments, the alkylene oxide recovery column 200 can have a polygonal shape and can be oriented in a horizontal manner. In addition, the alkylene oxide recovery column 200 can have a broad range of sizes. For example, the column 200 having a cylindrical shape can have a diameter ranging from about 65 centimeters to about 6 meters, or more than about 6 meters, and a height ranging from about 6 meters to about 60 meters, or more.

In addition, as will be appreciated by one skilled in the art, the alkylene oxide recovery column 200 can be made of any material commonly used in making such columns, for example, steel. In some embodiments, the column 200 can be jacketed (not shown), wherein a space between the jacket and the column 200 can be flushed with an inert gas, for example, carbon dioxide, nitrogen, and/or argon. As will be appreciated, jacketing the column 200 can additionally protect against external sources of ignition which can initiate explosive decomposition of alkylene oxide. In the illustrated embodiment, the alkylene oxide recovery column 200 is a vertically oriented cylindrical column made of stainless steel.

The operating conditions within the alkylene oxide recovery column 200 can be adjusted according to processing conditions. For example, the column 200 may be operated at a wide range of pressures, ranging from sub-atmospheric (i.e., vacuum), to near atmospheric, to super atmospheric. In practice, the general operating pressure of the column 200 can be selected during system design, although there is some flexibility to adjust the pressure of the column 200 during normal operation. The design operating pressure of the column 200 can range from about 60 kilopascal (kPa) to about 2,200 kPa, preferably from about 80 kPa to about 1,100 kPa, and more preferably from about 200 kPa to about 450 kPa.

In addition, there can be a gradient in pressure across the column 200, with the highest pressure in the stripping section 202 and the lowest pressure in the reabsorption region 204. This gradient may be a gradual change across the column 200 and/or various sections of the column 200, or may be an abrupt pressure change. As one skilled in the art will appreciate, the pressure drop can be primarily generated across the separation stages (e.g., trays and/or packing) in the stripping section 202, as discussed further herein, across the condensing zone 205, as discussed herein, and/or across the separation stages in the reabsorption region 204, as discussed further herein. In addition, the pressure drop can be influenced by design and operational factors, such as vapor flux, liquid flux, the number of separation stages (e.g., trays and/or packing height and/or the choice of packing) and/or condenser design, among others. The pressure gradient in the column can range from about 1 kPa to about 1,000 kPa, preferably from about 3 kPa to about 500 kPa, and more preferably from about 5 kPa to about 300 kPa.

The alkylene oxide recovery column 200 may also be operated at a wide range of temperatures. In practice, the operating temperature of the column 200 can be selected during system design, although there can be significant variation in the column 200 temperature during operation. In addition, there can be a temperature gradient present in the column 200, with the highest temperature in the stripping section 202 and the lowest temperature in the reabsorption region 204. This gradient may be a gradual change across the column 200 and/or various sections of the column 200, or may be an abrupt temperature change. The operating temperature of the stripping section 202 can range from about 40° C. to about 200° C., preferably from about 60° C. to about 160° C., and more preferably from about 80° C. to about 140° C. The operating temperature of the condensing zone 205 can range from about 0° C. to about 140° C., preferably from about 3° C. to about 100° C., and more preferably from about 5° C. to about 60° C. The operating temperature of the reabsorption region 204 can range from about 10° C. to about 120° C., preferably from about 20° C. to about 100° C., and more preferably from about 25° C. to about 80° C.

As can be appreciated by one skilled in the art, the operating temperature of the column 200, the operating pressure of the column 200, and the composition of the feed stream 206, discussed herein, can all be highly interdependent. Also, certain sections of the column 200 can be impacted by other variables, such as the reabsorption water temperature, desired reflux ratio, pressure drop, the presence of other feed inlets and/or outlets, and/or the presence of auxiliary heaters and/or coolers. In design and operation, these variables can be optimized to provide a balance between the operating cost of the stripping section 202, the operating cost of the reabsorption region 204, the operating cost of the condensing zone 205, and the overall column 200 capital cost. For instance, the stripping section 202 can have the lowest operating cost when run at lower pressure; however, the reabsorption region 204 can have the lowest operating costs when operated at high pressure. Other factors may also impact the chosen system operating pressure, such as column cost, (e.g., higher pressure columns lead to more capital cost) heat source availability (e.g., the heat source required to drive the stripping section 202 to a certain temperature), or cooling source availability (e.g., the cooling source required to achieve the operating temperature in the condensing zone 205). In addition, often the optimum economic balance is related to heat integration requirements or other integrations requirements with other parts of the plant.

The alkylene oxide recovery column 200 includes a stripping section 202, a condensing zone 205 including at least two condensers 207, 209 configured in series above the stripping section 202, and a reabsorption region 204. In certain embodiments, the stripping section 202 can be located at a lower portion of the alkylene oxide recovery column 200 and the reabsorption region 204 can be located above the last of the at least two condensers in the condensing zone 205 of the alkylene oxide recovery column 200.

In some embodiments, the stripping section 202 can be operated at a pressure in a range from about 130 kPa to about 150 kPa and a temperature in a range of from about 100° C. to about 120° C., while the reabsorption region 204 can be operated at a pressure in a range of from about 110 kPa to about 130 kPa and a temperature in a range of from about 30° C. to about 50° C.

As will be appreciated by one skilled in the art, the design and operation of the column 200 can depend on the composition of the feed stream 206 as well as the composition of the desired products, among other things. In some instances, for example, with a binary component feed, analytical methods such as the McCabe Thiele method or the Fenske equation can be used to determine the number of equilibrium stages to use to achieve the desired separation. For a multi-component feed stream, simulation models can be used for both design (e.g., to determine the number of equilibrium stages needed in order to achieve the desired separation) and operation (e.g., to determine the optimum operating conditions). In addition, once the number of equilibrium stages is determined, one skilled in the art can use routine experimentation to determine the actual number of separation stages (e.g., the actual number of trays or height of packing) to use in a column to achieve the desired separation.

The column 200 of the present disclosure can be operated with distillation trays (plates), packing, or a combination of distillation trays and packing. The distillation trays can be of the types commonly found in distillation columns, such as sieve plates, bubble-cap plates, or valve plates, among others. In some embodiments, the distance between each tray can vary. In addition, in embodiments using packing, the packing material can be random dumped packing such as, for example, Raschig rings, Pall rings, or Bialecki rings in metal or ceramic. The packing material can also be structured sheet-metal packing such as those known and commercially available for example under the designations Gempak® (Koch-Glitsch, LP, Dallas, Tex., U.S.A) and/or Mellapak® (Gebr. Sulzer, Winterthur, Switzerland).

In embodiments where random packing is employed, the total required height of packing to provide the required number of separation stages can be determined by multiplying the number of calculated equilibrium stages by the Height Equivalent to a Theoretical Plate, or HETP. The HETP is a value of the height of packing that will give the same separation as an equilibrium stage. As known to one skilled in the art, the HETP can vary depending on the type of packing selected.

In some embodiments, the total height of packing can be split into one or more zones with vapor-liquid redistributors in between the zones, for example, to accommodate height limitations due to packing structural integrity or to accommodate feed streams or product streams. In some embodiments, packing may offer the advantage of a lower pressure drop as compared to trays, although consideration must also be given to the cost difference arising from the choice of trays versus packing.

The stripping section 202 of the column 200 of the present disclosure can be operated in such a way as to include between 4 and 14 separation stages, preferably between 6 and 12 separation stages, and more preferably between 7 and 11 separation stages. As such, the stripping section 202 can include about 6 to about 25 separation stages. In some embodiments, when trays are used the distance between each tray can vary, where the distance between each tray is optimized for the best separation of the feed stream 206 components at the specific temperature and pressure of each tray.

In some embodiments, each separation stages can be at a different temperature and pressure, wherein the lower portion of the stripping section 202 can have the highest pressure and temperature. In some embodiments, with upward progression in the stripping section 202, temperature and pressure can decrease at one or more succeeding separation stages. In some embodiments, the vapor-liquid equilibrium of the feed stream 206 reacts in a unique way to the different pressure and temperature conditions at each of the separation stages.

In some embodiments, the stripping section 202 can have a number of components, including inlets and outlets. The shape or structure of the inlets and outlets can be modified to affect and/or control the flow therethrough. For example, an inner surface of the inlets/outlets can be rifled. The rifling can spin the fluid flowing out through the ends and enhance mixing. In FIG. 2, a feed inlet 211 is provided at an upper portion of the stripping section 202 to introduce a feed stream 206 into the stripping section 202.

In some embodiments, the feed stream 206 includes alkylene oxide and water. Non-limiting examples of other compounds in the feed stream 206 include methane, carbon dioxide, oxygen, and/or alkylene, among others. In some embodiments, the composition of the feed stream 206 is about 1 weight percent to about 5 weight percent alkylene oxide, 0 weight percent to about 0.03 weight percent alkane (e.g., methane), about 0 weight percent to about 0.03 weight percent carbon dioxide, about 0 weight percent to about 0.015 weight percent oxygen, about 0 weight percent to about 0.06 weight percent alkylene with the remaining portion being made up of water, with all weight percents being based on the total weight of the feed stream 206. In one embodiment, the composition of the feed stream 206 is about 3 weight percent ethylene oxide, about 0.02 weight percent methane, about 0.02 weight percent carbon dioxide, about 0.01 weight percent oxygen, about 0.04 weight percent ethylene with the remaining portion being made up of water, with all weight percents being based on the total weight of the feed stream 206. The feed stream 206 may further contain impurities, namely, chlorine containing organic compounds and oxygenated hydrocarbons. In certain embodiments, the feed stream 206 is of two phases, a liquid phase and a vapor phase.

The feed stream 206 produced from absorbing the dilute alkylene oxide mixture in the absorber can be introduced to the stripping section 202 of column 200. In certain embodiments, steam or hot water can be introduced as a first gaseous stream 208 into the stripping section 202 to contact the feed stream 206 in a counter current fashion.

In some embodiments, steam can be generated within the stripping section 202 by making use of a heating mechanism placed internally or externally to the column 200. For example, a steam heated reboiler can be employed to heat water in the bottom of the stripping section 202 and boil it.

In some embodiments, the first gaseous stream 208 strips alkylene oxide from the feed stream 206 by converting a portion of the feed stream 206 into a first gas phase 210 portion. As used herein, the first "gas phase portion" 210 is the portion of the feed stream 206 that undergoes a phase change and subsequently enters a condenser, as discussed herein.

In embodiments of the present disclosure, the first gas phase portion 210 enters the first condenser 207. The remaining portion 212 of the feed stream 206 includes water and traces of alkylene oxide, as well as other compounds. The remaining portion 212 of the feed stream 206 can be removed from the bottom portion of the stripping section 202 and routed back to the absorber, as discussed herein, to collect more alkylene oxide to be brought back to the column 200 in the feed stream 206. In some embodiments, the alkylene oxide in the remaining portion 212 of the feed stream 206 routed to absorber can be in a range from about zero to about 1,000 mole ppm (parts per million) alkylene oxide.

The stripping section 202 can further include at least one inlet (not shown) to introduce an input stream containing alkylene and/or alkylene oxide from an alkylene oxide pre-recovery or post-recovery process to maximize the efficiency as well as the economics of alkylene oxide production and recovery. As discussed earlier, the recovery column 200 can be part of the alkylene oxide-alkylene glycol manufacturing unit including alkylene oxide production, concentration, purification, and optionally, glycol formation.

As discussed herein, the stripping section 202 can be located below the condensing zone 205 including at least two condensers 207, 209 in series. By including a condensing zone 205 with at least two condensers in series it is possible to recover increased yields of purified alkylene oxide, as compared to an identical process but for the condensing zone 205. The impurity reduction can minimize unwanted chemical reactions in the subsequent glycol reaction processes, and can lead to improved ultraviolet absorbance and color in the purified glycol products.

In some embodiments, the first gas phase portion 210 of the feed stream 206 can flow from the stripping section 202 to the first condenser 207 of the condensing zone 205 to cool and partially condense the first gas phase portion 210, producing a liquid reflux stream 222 and a second gas phase portion 224. In some embodiments, the first gas phase portion 210 of the feed stream 206 entering the first condenser 207 of the condensing zone 205 can have a temperature ranging from about 80° C. to about 110° C., preferably ranging from about 90° C. to about 100° C.

In some embodiments, the first condenser 207 in the condensing zone 205 can include, for example, a cooling water stream (not shown) flowing in a counter current fashion to the first gas phase portion 210 of the feed stream 206 to cool and partially condense the first gas phase portion 210. As illustrated in FIG. 2, the first condenser 207 in the condensing zone 205 can be integral to the column 200 and can be located above the stripping section 202. In some embodiments, the first condenser 207 in the condensing zone 205 can be external to the column 200 and configured in series with the stripping section 202.

In some embodiments, the first condenser 207 in the condensing zone 205 can be a reflux condenser, where the first condenser 207 in the condensing zone 205 returns condensed vapors directly to the stripping section 202, while uncondensed gases pass through the first condenser 207 in the condensing zone 205. In some embodiments, a portion of heat removed from the first condenser 207 in the condensing zone 205 can be employed in other parts of alkylene oxide production processes.

The first condenser 207 in the condensing zone 205 can also include a first chimney tray 226 located above the first condenser 207 in the condensing zone 205 such that the second gas phase portion 224 can flow through a chimney 228 and enter the second condenser 209 in the condensing zone 205, as discussed herein. As used herein, a "chimney tray" is a tray designed in such a way to allow vapor (e.g., second gas phase portion 224) to rise through it, while preventing liquid from passing down through the tray 226. In some embodiments, the first chimney tray 226 can be formed of a solid tray with a chimney 228, or standpipe, topped by a "hat" to keep liquid from raining down through the standpipe. A "stand pipe" as used herein, refers to an open pipe which extends through the first chimney tray 226 for a distance above the first chimney tray 226 so that liquid can collect on the first chimney tray 226 without flowing back into the stripping section 202. As used herein, a "hat" refers to a cover that is loosely connected to the standpipe that can allow vapor to flow up and out of the of the standpipe, while preventing condensed liquid, for example, from the second condenser 209 in the condensing zone 205, from entering the standpipe and draining into the first condenser 207 in the condensing zone 205. As will be appreciated by one skilled in the art, the chimney 228 can additionally enhance the distribution of an up-flowing vapor (e.g., second gas phase portion 224) through a packed column, where the packing is one of trays, dumped packing, structured packing, or a mixture of trays and packing.

In some embodiments, the chimney tray 226 can be designed to allow liquid on the chimney tray 226 to overflow into the first condenser 207 in the condensing zone 205 in an upset condition. As used herein, the term "upset conditions" is defined as the conditions in which there is a disturbance and/or deviation from normal functioning of the process.

As shown in FIG. 2, a second gaseous stream 230 can be introduced to the column 200 above the first chimney tray 226 to strip light gases, such as carbon dioxide and/or oxygen, from a first aqueous solution 232 collected on the first chimney tray 226, as discussed further herein. In some embodiments, the second gaseous stream 230 can be steam. Stripping the first aqueous solution 232 can produce a gas phase portion 234 of the first aqueous solution 232 that includes light gases such as carbon dioxide and oxygen. As will be appreciated by one skilled in the art, the gas phase portion 234 of the first aqueous solution 232 can flow upward with the second gas phase portion 224 into the second condenser 209 in the condensing zone 205.

The first aqueous solution 232 can be removed in the condensing zone 205 from the column 200 as a first alkylene oxide stream 236 at a side take-off located adjacent to where the liquid collects on the chimney tray 226. In some embodiments, the first alkylene oxide stream 236 removed from the condensing zone 205 in the column 200 can be routed to a glycol reactor to convert the first alkylene oxide stream 236 to alkylene glycol. The first alkylene oxide stream 236 can also be routed for further purification or for further reaction.

As illustrated in FIG. 2, the second gas phase portion 224 can flow from the first condenser 207 in the condensing zone 205 to the second condenser 209 in the condensing zone 205 to cool and partially condense the second gas phase portion 224 to produce an alkylene oxide rich vapor stream 235 and the first aqueous solution 232, as discussed herein. The second gas phase portion 224, in some embodiments, can enter the second condenser 209 in the condensing zone 205 at a temperature ranging from about 20° C. to about 60° C., preferably from about 30° C. to about 40° C.

In some embodiments, the second condenser 209 in the condensing zone 205 can include, for example, a cooling water stream (not shown) flowing in a countercurrent fashion to the second gas phase portion 224 to cool and partially condense the second gas phase portion 224. In some embodiments, the cooling water stream can be chilled water or brine.

As illustrated in FIG. 2, the second condenser 209 in the condensing zone 205 can be integral to the column 200 and can be located above the first condenser 207 in the condensing zone 205. In some embodiments, the second condenser 209 in the condensing zone 205 can be external to the column 200 and can be configured in series with the first condenser 207 in the condensing zone 205 and stripping section 202. In addition, the second condenser 209 in the condensing zone 205 can be a reflux condenser, wherein the second condenser 209 in the condensing zone 205 returns condensed vapors to the first condenser 207 in the condensing zone 205 to form the first aqueous solution 232, while uncondensed gases pass through the second condenser 209 in the condensing zone 205 to the reabsorption region 204.

Similar to the first condenser 207 in the condensing zone 205, the second condenser 209 in the condensing zone 205 can include a second chimney tray 238 including a second chimney 240. As discussed herein, the second chimney tray 238 can allow vapor (e.g., the alkylene oxide rich vapor stream 235) to pass into the reabsorption region 204 while allowing condensed liquids formed in the reabsorption region 204 to collect on the second chimney tray 238.

As illustrated in FIG. 2, the alkylene oxide rich vapor stream 234 can enter the reabsorption region 204 by passing through the second chimney 240. For example, the alkylene oxide rich vapor stream 235 can enter the lower portion of the reabsorption region 204 from the second condenser 209.

The reabsorption region 204, as illustrated, has a mass transfer section consisting of separation stages (e.g., trays, dumped packing, structured packing or a mixture of trays and packings), as discussed herein with reference to the mass transfer section in the stripping section 202. The reabsorption region 204 of the column 200 can be operated in such a way as to include between 2 and 10 separation stages, preferably between 3 and 9 separation stages, and more preferably between 4 and 8 separation stages.

A water inlet can be provided in the reabsorption region 204 to introduce a water stream 242. The water stream 242, in some embodiments, can be process water or raw water. In some embodiments, the water stream 242 can be a recycle stream from one or more of the alkylene oxide production processes. The water stream 242, can be provided to the reabsorption region 204 at an upper portion of the reabsorption region 204.

In some embodiments, the water stream 242 can reabsorb at least some of the alkylene oxide in the alkylene oxide rich vapor stream 235 to form a second aqueous solution 244. As will be appreciated, reabsorbing the alkylene oxide in the alkylene oxide rich vapor stream 235 to form the second aqueous solution 244 can require a quantity of water stream 242 sufficient to reabsorb a desirable amount of alkylene oxide. According to embodiments of the present disclosure, reabsorbing at least some of the alkylene oxide in the alkylene oxide rich vapor stream 235 can include reabsorbing about 1 percent to about 80 percent of the alkylene oxide from the alkylene oxide rich vapor stream 235. In various embodiments, reabsorbing at least some of the alkylene oxide in the alkylene oxide rich vapor stream 235 can include reabsorbing about 3 percent to about 65 percent of the alkylene oxide from the alkylene oxide rich vapor stream 235.

In some embodiments, the second aqueous solution 244 produced from reabsorbing alkylene oxide in the alkylene oxide rich vapor stream 235 can include alkylene oxide in the range of about 2 weight percent to about 10 weight percent, based on total weight of the second aqueous solution 244. In certain embodiments, the reabsorption region 204 can include a second side take-off located in the lower portion of reabsorption region 204 to remove the second aqueous solution 244 as a second alkylene oxide stream 246 from the column 200.

In some embodiments, the second side take-off can be located at a side wall of the reabsorption region 204. In some embodiments, the second side take-off can be in physical communication with a glycol unit reactor. As such, the second aqueous solution 244 can be transferred to the glycol unit reactor, where alkylene oxide is converted to alkylene glycol by reaction with water.

In some embodiments, the second alkylene oxide stream 246 can include about 10 weight percent of alkylene oxide, based on total weight of the second alkylene oxide stream 246. In addition, the temperature of the second alkylene oxide stream 246 exiting the column can vary depending upon the process conditions (for example, water stream temperature, rate of the water stream flow, the amount of gas injected in gaseous stream, etc.). In some embodiments, the temperature of the second aqueous solution 246 can be about 50° C.

In various embodiments, the second take-off can be in physical communication with an alkylene oxide purification unit. The alkylene oxide purification unit can further refine the second aqueous solution 246 by removing impurities such as aldehydic impurities and/or light gases (e.g., methane, carbon dioxide, and oxygen).

In the illustrated embodiment of FIG. 2, the reabsorption region 204 can include a gaseous stream inlet 248 to introduce a second gaseous stream 250. In some embodiments, the second gaseous stream 250 includes steam. The gaseous stream 250 can strip light gases, such as carbon dioxide and oxygen, from the second aqueous solution 246 to form a gas phase light impurities fraction 252. As will be appreciated, the gas phase light impurities fraction 252 flows upward with the alkylene oxide rich vapor stream 235 that has not been condensed in the second condenser 209 in the condensing zone 205.

In some embodiments, the gas phase light impurities fraction 252 that is formed in the reabsorption region 204 can flow to the upper portion of the column 200. The gas phase light impurities fraction 252 can then be removed from the column 200 through a top outlet located at an upper portion of the reabsorption region 204.

In some embodiments, the column 200 can include a vent gas compressor 254 which can compress the gas phase light impurities fraction 252 to produce a compressed gas phase light impurities fraction 256 and a condensed liquid 258. In some embodiments, the compressed gas phase light impurities faction 256 can be recycled back to the alkylene oxide reactor. In addition, the condensed liquid 258 can be recycled back to the stripping section 202 of the column 200 to recover the alkylene oxide and water that can be present in the condensed liquid 258.

Embodiments of the present disclosure can improve the removal of aldehydic impurities by including the first and second condensers 207, 209 in series between the stripping section 202 and reabsorption region 204 to form the condensing zone 205. As such, the second aqueous solution 244 produced in the reabsorption region 204 can be sent directly to an alkylene glycol reactor.

For the various embodiments, the ethylene oxide recovery according to the present disclosure can be processed to provide further downstream products, such as, for example, 1,2-diols, 1,2-diol ethers, 1,2-carbonates, and alkanolamines. Since the present disclosure provides improvements to the separation and purity of the ethylene oxide, it is contemplated that the improvements provided herein will carry forward to provide improvements to these downstream processes and/or products. Improved methods for the production of 1,2-diols, 1,2-carbonates, 1,2-diol ethers and alkanolamines are thus also provided herein.

The conversion of ethylene oxides into 1,2-diols or 1,2-diol ethers may comprise, for example, reacting the ethylene oxide with water, suitably in the presence of an acidic or basic catalyst. For example, for preferential production of the 1,2-diol over the 1,2-diol ether, the ethylene oxide may be reacted with a tenfold molar excess of water, in a liquid phase reaction in the presence of an acid catalyst, e.g., 0.5-1.0 wt % sulfuric acid, based on the total reaction mixture, at 50-70° C. at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternatively, 1,2-diol ethers may be prepared by converting the ethylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of ethylene oxide recovered according to the present disclosure into alkanolamines may comprise, for example, reacting the ethylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

In order to indicate still more fully the nature of the present disclosure, the following examples of typical procedures are set forth, unless otherwise indicated, it being understood that these examples are presented as illustrative only and are not intended to limit the scope of the disclosure.

Specific Embodiments of the Present Disclosure

The following examples are performed using ASPEN 2004.1 simulations and are provided by way of illustration only and should not be limited to construe the scope of the disclosure. Mass and energy balances are performed using AspenTech's Aspen Plus 2004.1 from Aspen Technology, Inc. (Cambridge, Mass. USA), a commercially available simulation package commonly used throughout the chemical industry. Common components present in a typical ethylene oxide/ethylene glycol production facility are included in the component list, including ethylene oxide, ethylene, oxygen, argon, carbon dioxide, methane, water, ethane, nitrogen, monoalkylene glycol, ethylene glycol, triethylene glycol, tetraethylene glycol and acetaldehyde. The base method used in the simulation is the UNIQUAC/Redlich-Kwong equation of state with Henry's Law.

The reabsorber/light gas strippers are modeled using a single six-separation stage RadFrac block. Reabsorbing water is fed to the top separation stage, separation stage 1, and the feed stream is fed to separation stage 5. Stripping steam is fed to separation stage 6. The tails liquid exits the base of the column at separation stage 6 and the process gas exits the top of the column at separation stage 1. Reabsorbing water, steam flows, condenser outlet temperatures and heat input to the stripper are adjusted to give the desired light gas concentration and amount of ethylene oxide in the liquid tails stream.

EXAMPLE 1

In this example, a computer simulation is conducted employing the process conditions of the disclosure wherein a second condenser (chilled condenser), chimney tray, and stripping section is added to the stripper section/reabsorbing region as depicted in FIG. 1. The first condenser forms a reflux with the stripping section. The vapor leaving the first condenser passes through a chimney tray and enters the second condenser. Condensed liquid from the second condenser flows back down the column around the chimney through a packed portion in the annulus. Process steam is fed below the packed portion to strip out dissolved light gases in the condensed liquid. The stripped gases are forced back up the column through the second condenser. The liquid stripped of light gases is collected on the first chimney tray and exits the column to be used as the feed to an ethylene oxide purification column. The gases that pass through the top of the second condenser pass through second chimney tray and enter the reabsorption region. Water flows down countercurrently with the gases, absorbing ethylene oxide and some of the light gases. The vapor leaving the top of the column is predominantly light gases, steam, and trace amounts of ethylene oxide and impurities. The liquid exiting the reabsorption region flows downward into the small packed portion in the annulus surrounding the chimney tray. Steam is fed below the packed portion to strip light gases. The stripped liquid is collected on the second chimney tray and it is fed to the glycol reaction system. In this example, about 65 percent of the ethylene oxide fed to the stripper is collected as condensed liquid and fed to the ethylene oxide purification column. The values resulted from simulation are shown in Table 1.

TABLE 1

| kg/hr | Stripper Feed | Stripper Tails | To EO Column | Overhead stream | Water to Reabs region | EO/Water to glycol |
|---|---|---|---|---|---|---|
| Ethylene Oxide | 46,957 | 43.5 | 30,495 | 0 | 0 | 16,418 |
| Acetaldehyde | 4.2 | 0 | 3.1 | 0 | 0 | 1.1 |
| Ethylene Dichloride | 9.9 | 0 | 9.6 | 0 | 0 | 0.3 |
| Water | 1,411,641 | 1,410,724 | 887 | 51 | 219,575 | 223,023 |

EXAMPLE 2

In this example, a computer simulation is conducted employing the process conditions stripping section, a single condenser, and a reabsorbtion region. The column condenser forms a reflux with the stripping section. The gases that pass through the top of the condenser pass through a chimney tray and enter the reabsorbtion region. Water flows down countercurrently with the gases, absorbing ethylene oxide and some of the light gases into the water. The vapor leaving the top of the column is predominantly light gases, steam, and trace amounts of ethylene oxide and impurities. The liquid exiting the reabsorption region packing flows downward into the small packed portion in the annulus surrounding the chimney tray. Steam is fed below the packed portion to strip light gases. The stripped liquid is collected on the chimney tray and is fed so that 35 percent goes to the glycol reaction system and 65 percent goes to the EO purification system. The values resulted from simulation are shown in Table 2.

TABLE 2

| kg/hr | Stripper Feed | Stripper Tails | To EO Column | Overhead stream | Water to Reabs region | EO/Water to glycol |
|---|---|---|---|---|---|---|
| Ethylene Oxide | 46,957 | 43.5 | 30,494 | 0 | 0 | 16,420 |
| Acetaldehyde | 4.2 | 0 | 2.7 | 0 | 0 | 1.5 |
| Ethylene Dichloride | 9.9 | 0 | 6.4 | 0 | 0 | 3.5 |
| Water | 1,411,641 | 1,410,724 | 283499 | 48 | 431,813 | 152,653 |

As can be seen by the comparison of Examples 1 and 2, the amount of impurities (e.g., acetaldehyde and ethylene dichloride) in the glycol feed stream is much reduced in the process conditions described in Example 1. As discussed above, these impurities are undesirable in the feed to the glycol reactor since the impurities can reduce glycol quality. The reduction of the impurities in the feed stream to the glycol reactor (i.e., "EO/Water to Glycol") is due to the presence of the second condenser in the condensing zone, as described in embodiments herein. The second condenser allows the feed stream to be condensed and stripped an additional time, as compared to the column described in FIG. 1, providing an extra opportunity to remove impurities.

What is claimed:

1. A system to recover alkylene oxide, comprising:
    a stripping section located in an alkylene oxide recovery column to convert a feed stream that includes alkylene oxide and water to a first gas phase portion that includes alkylene oxide;
    a condensing zone that includes at least a first condenser and a second condenser configured in series such that:
        the first condenser partially condenses the first gas phase portion to produce a liquid reflux stream and a second gas phase portion that includes alkylene oxide, water, and light gases;
        the second condenser partially condenses the second gas phase portion to produce an alkylene oxide rich vapor stream and a first aqueous solution that includes alkylene oxide, water, and light gases; and
    a reabsorption region located in the alkylene oxide recovery column above the last of the at least two condensers, wherein an aqueous stream reabsorbs alkylene oxide from the alkylene oxide rich vapor stream to produce a second aqueous solution that includes alkylene oxide, water, and light gases.

2. The system of claim 1, further including a take-off located in a lower portion of at least one of the second condenser and the reabsorption region.

3. The system of claim 1, further including at least one gaseous stream inlet to introduce a gaseous stream to at least one of the second condenser and the reabsorption region to strip light gases from at least one of the first aqueous solution and the second aqueous solution to form at least one of a first and a second gas phase light impurities fraction; and an upper take-off located on the alkylene oxide recovery column to remove one or more gas phase light impurities fractions from the alkylene oxide recovery column.

4. The system of claim 1, where the stripping section includes a carbon dioxide stream from a carbon dioxide absorber that is collected with the light impurity fractions.

5. The system of claim 1, where the at least two condensers are integral with the alkylene oxide recovery column and located above the stripping section.

6. The system of claim 1, where the alkylene oxide rich vapor stream includes at least about 70 mole percent of alkylene oxide.

7. The system of claim 1, where the feed stream includes up to about 10 weight percent alkylene oxide, and further includes acetaldehyde in a range of about 0 to about 0.1 weight percent, methane in a range of about 0 to about 1 weight percent, carbon dioxide in a range of about 0 to about 1 weight percent, oxygen in a range of about 0 to about 1 weight percent, and alkylene in a range of about 0 to about 1 weight percent, based on total feed stream weight.

8. The system of claim 1, wherein the first aqueous solution includes about 50 to about 99 weight percent of alkylene oxide and the second aqueous solution includes up to about 10 weight percent of alkylene oxide.

9. The system of claim 1, further including a chimney tray located in the lower portion of the second condenser, where the first aqueous solution collects on the chimney tray while the second gas phase portion passes through the chimney of the chimney tray.

10. The system of claim 1, further including a chimney tray located in the lower portion of the reabsorption region, wherein the second aqueous solution collects on the chimney tray while the alkylene oxide rich vapor stream passes through the chimney of the chimney tray.

11. A process for recovering alkylene oxide comprising:
introducing a feed stream that includes alkylene oxide to an alkylene oxide recovery column that includes a stripping section, a condensing zone and a reabsorption region, wherein the condensing zone includes at least a first condenser and a second condenser configured in series;
stripping at least a portion of alkylene oxide from the feed stream to produce a first gas phase portion, wherein the first gas phase portion flows from the stripping section to the reabsorption region through the condensing zone;
partially and progressively condensing the first gas phase portion in the first condenser of the condensing zone into a liquid reflux stream and a second gas phase portion;
condensing the second gas phase portion in the second condenser of the condensing zone into an alkylene oxide rich vapor stream including alkylene oxide and a first aqueous solution; and
reabsorbing at least some of the alkylene oxide from the alkylene oxide rich vapor stream into an aqueous stream in the reabsorption region to produce a second aqueous solution.

12. The process of claim 11, further including stripping light gases from at least one of the second aqueous solution by introducing a gaseous stream to form a gas phase light impurities fraction.

13. The process of claim 11, further including removing a gas phase light impurities fraction as a top exit stream from the alkylene oxide recovery column.

14. The process of claim 11, where the gaseous stream from the first condenser is condensed by the second condenser to produce the first aqueous solution which is sent to an alkylene oxide purifying column.

15. The process of claim 11, where the gaseous stream from the second condenser is absorbed by an aqueous stream in the reabsorption region to produce the second aqueous solution which is sent to a glycol reactor.

16. The process of claim 11, where the aqueous solution from the second condenser includes about 50 to about 99 weight percent of alkylene oxide.

17. The process of claim 11, where the aqueous solution from a lower portion of reabsorption region includes up to about 10 weight percent of alkylene oxide.

18. The process of claim 11, where the alkylene oxide is ethylene oxide or propylene oxide.

19. The process of claim 18, where the process includes converting the ethylene oxide to ethylene glycol in a glycol reactor.

20. The process of claim 18, where the ethylene glycol is at least one of mono ethylene glycol, diethylene glycol, and triethylene glycol.

* * * * *